United States Patent [19]

Wang et al.

[11] Patent Number: 5,443,073
[45] Date of Patent: Aug. 22, 1995

[54] SYSTEM AND METHOD OF IMPEDANCE CARDIOGRAPHY MONITORING

[75] Inventors: Xiang Wang, Lansdale; Hun H. Sun, Blue Bell, both of Pa.

[73] Assignee: Drexel University, Philadelphia, Pa.

[21] Appl. No.: 61,793

[22] Filed: May 13, 1993

Related U.S. Application Data

[63] Continuation-in-part of Ser. No. 834,425, Feb. 12, 1992, Pat. No. 5,309,917, which is a continuation-in-part of Ser. No. 758,034, Sep. 12, 1991, abandoned.

[51] Int. Cl.⁶ .............................................. A61B 5/029
[52] U.S. Cl. ..................................... 128/713; 128/734
[58] Field of Search ........ 128/671, 672, 687, 693–696, 128/713, 734

[56] References Cited

U.S. PATENT DOCUMENTS

| Re. 30,101 | 9/1979 | Kubicek et al. | 128/713 |
|---|---|---|---|
| 3,149,627 | 9/1964 | Bagno . | |
| 3,340,867 | 9/1967 | Kubicek et al. . | |
| 3,452,743 | 7/1969 | Rieke . | |
| 3,570,474 | 3/1971 | Jonson . | |
| 3,730,171 | 5/1973 | Namon . | |
| 3,742,936 | 7/1973 | Blanie et al. . | |
| 3,835,839 | 9/1974 | Brown . | |
| 3,835,840 | 9/1974 | Mount . | |
| 3,847,142 | 11/1974 | Williams, Jr. et al. . | |
| 3,871,359 | 3/1975 | Pacela . | |
| 3,874,368 | 4/1975 | Asrican . | |
| 3,882,851 | 5/1975 | Sigworth . | |
| 3,976,052 | 8/1976 | Junginger et al. . | |
| 3,994,284 | 11/1976 | Voelker . | |
| 3,996,925 | 12/1976 | Djordjevich . | |
| 4,204,545 | 5/1980 | Yamakoshi | 128/693 |
| 4,205,688 | 6/1980 | Hauser et al. | 128/694 |
| 4,258,720 | 3/1981 | Flowers | 128/694 |
| 4,305,400 | 12/1981 | Logan | 128/670 |
| 4,422,458 | 12/1983 | Kravath | 128/671 |
| 4,432,374 | 2/1984 | Osanai | 128/694 |
| 4,437,469 | 3/1984 | Djordjevich et al. | 128/672 |
| 4,450,527 | 5/1984 | Sramek | 364/415 |
| 4,548,211 | 10/1985 | Marks | 128/694 |
| 4,562,843 | 1/1986 | Djordjevich et al. | 128/672 |
| 4,641,260 | 2/1987 | Fukukita et al. | 364/737 |
| 4,649,932 | 3/1987 | Smith | 128/734 |
| 4,676,253 | 6/1987 | Newman et al. | 128/693 |
| 4,733,670 | 3/1988 | Hays et al. | 128/693 |
| 4,757,824 | 7/1988 | Chaumet | 128/716 |
| 4,805,621 | 2/1989 | Heinze et al. . | |

(List continued on next page.)

OTHER PUBLICATIONS

Kizakevich et al, "Continuous Noninvasive Cardiac Monitoring etc.", *Proc. Symp. on Computers In App. Med. Care*, 1977 pp. 325–336.

(List continued on next page.)

Primary Examiner—Lee S. Cohen
Assistant Examiner—Jeffrey R. Jastrzab
Attorney, Agent, or Firm—Panitch Schwarze Jacobs & Nadel

[57] ABSTRACT

Cardiac monitoring is disclosed in which thoracic impedance and EKG signals are gathered and processed for improved resolution and accuracy. EKG signals are adaptively processed by digitizing, filtering, differentiating and raising the resultant differential by a power greater than one to emphasize changes in the slope of the EKG signal. Blocks of the thus processed EKG data are analyzed to identify peak amplitude and to compare spacing between peak amplitudes adaptively to more accurately identify R wave peaks. Stroke volume is determined from a thoracic impedance signal and its time derivative. Preferably, a time-frequency distribution is taken of the time derivative thoracic impedance signal after low- and high-pass filtering to identify B and X wave events in the signal which are used to determine ventricular ejection time and $dZ/dt_{min}$ for a determination of heart stroke volume by conventional methods. Alternatively, stroke volume is determined by a new relationship between a product of a pair of absolute impedances simultaneously sensed on opposing sides of a patient's heart at the peak of a heartbeat.

26 Claims, 6 Drawing Sheets

U.S. PATENT DOCUMENTS

| | | |
|---|---|---|
| 4,807,638 | 2/1989 | Sramek .................................... 128/672 |
| 4,823,797 | 4/1989 | Heinze et al. . |
| 4,836,214 | 6/1989 | Sramek .................................... 128/693 |
| 4,870,578 | 9/1989 | Vysin et al. ...................... 364/413.05 |
| 4,905,705 | 3/1990 | Kizakevich et al. ................. 128/696 |
| 4,979,110 | 12/1990 | Albrecht et al. ................ 364/413.03 |
| 5,025,784 | 6/1991 | Shao et al. ........................... 128/419 |
| 5,046,504 | 9/1991 | Albert et al. ......................... 128/696 |
| 5,101,828 | 4/1992 | Welkowitz et al. ................. 128/668 |
| 5,103,828 | 4/1992 | Sramek .................................... 128/668 |
| 5,109,862 | 5/1992 | Kelen et al. ........................... 128/702 |
| 5,178,151 | 1/1993 | Sackner .................................. 128/672 |
| 5,178,154 | 1/1993 | Ackmann et al. ................... 128/713 |

OTHER PUBLICATIONS

Kizakevich et al, "An Automated System for Systolic Time Interval Analysis", Proc. Dig. Eq. Comp. Users Soc., 1976, pp. 795–798.

Gollan et al, "Continuous Electrode Monitoring etc.", British Heart Journal, 1978, pp. 1390–1396.

Geddes, "The Measurement of Cardiac Output and Blood Flow", from Cardiovascular Devices and Their Applications, pp. 100–135.

Miyamoto et al, "Continuous Determination of Cardiac Output, etc.", Med. & Biol. Eng. & Computing, 1981, pp. 638–644.

Miyamoto et al, "Automatic Determination of Cardiac Output, etc." Proc. 5th Int'l Conf. on Electr. Bio-Impedance, 1981, pp. 45–48.

Miyamoto et al, "Automatic Determination of Cardiac Output, etc." Biotelemetry Patient Monitoring, 1981, pp. 189–203.

Sramek et al, "Stroke Volume Equation etc.", Proc. 6th Int'l Conf. on Electr. Bioimpedance, 1983, pp. 1–2.

Sramek, "Noninvasive Technique for Meas. of Cardiac Output, etc." Proc. 5th Int'l Conf. on Electr. Bioimpedance, 1981, pp. 39–42.

Kubicek et al, "Development and Evaluation of an Impedance Cardiac Output System", Aerospace Medicine, 1966, pp. 1208–1212.

Kubicek et al, "The Minnesota Impedance Cardiograph–Theory and Applications", Biomed. Eng. 1974, pp. 410–416.

Photocopy of Article "Digital Enhancement of the Peripheral Admittance Plethysmogram", L. A. Marks, *IEEE Transactions on Biomedical Engineering*, vol. BME–34, No. 3, Mar. 1987, 7 pages.

Photocopy of Instruction manual, "Minnesota Impedance Cardiograph–A Noninvasive System to Monitor Cardiovascular Pamameters", 4 sheets, Surcom, Inc., 4180 Edmund Boulevard, Minneapolis, Minn. 55406.

Photocopy of article "Mapping the Cardiogenic Impedance Signal on the Thoracic Surface", R. P. Patterson et al., *Medical & Biological Engineering & Computing*, May 1990, 5 pages.

B. Bo Sramek, "Cardiac Output by Electrical Impedance", *Medical Electronics*, Apr. 1982, pp. 93–97.

B. Bo Sramek, "Electrical Bioimpedance", *Medical Electronics*, Apr. 1983, pp. 95–105.

SYSTEM AND METHOD OF IMPEDANCE CARDIOGRAPHY MONITORING

RELATED APPLICATION

This is a continuation-in-part of U.S. patent application Ser. No. 07/834,425, filed Feb. 12, 1992 now U.S. Pat. No. 5,309,917, which is a continuation-in-part of application Ser. No. 07/758,034, filed Sep. 12, 1991 now abandoned, each of which is hereby incorporated by reference herein in its entirety.

FIELD OF THE INVENTION

The invention relates more specifically to continuous heart rate and hemodynamic monitoring.

BACKGROUND OF THE INVENTION

Cardiac monitoring to which the present invention relates includes both the determination of heart rate (HR) from electrocardiogram (EKG) signals and the determination of heart stroke volume (SV) from thoracic impedance signals, from which cardiac output (CO) can be estimated.

Heart rate can be determined in a number of ways. The phonocardiogram is considered among the most accurate methods of determining heart rate. However, due to the practical difficulties in using it, the phonocardiogram method is generally not employed for any continuous or long-term monitoring.

Heart rate is most typically determined by the electrocardiogram (EKG). The analog EKG signal typically displays electrocardial events as perturbations referred to as waves. The heartbeat is most clearly reflected in the EKG signal as an R wave peak between a pair of adjoining Q and S wave valleys. The basic and commonly used method of automatically identifying the QRS wave pulses in point is the threshold method in which the rate of voltage change between consecutive data points of the EKG signal is monitored and compared with a threshold value. Slopes exceeding the threshold value are deemed to be associated with a portion of the QRS pulse. While this method commonly detects the interval between consecutive R waves successfully more than eighty percent of the time, it typically has difficulty in dealing with sources of irregular signal components such as pacemakers, muscle noise, 60 Hz interference as well as nearby T or P waves which may also be associated with significant slope changes.

Hemodynamic monitoring of the heart can provide very valuable physiological information regarding the functional state of the myocardium, which is intimately related to its mechanical behavior. The quantitative measurement of blood flow, or the cardiac output (CO), is one of the most useful parameters in assessing cardiac capability, but it is also one of the most difficult to measure. It cannot be accomplished with the electrocardiogram (EKG) which does not reflect the real pumping action of the heart.

Both invasive and non-invasive methods are available for measurement of cardiac output. The invasive methods are considered the most accurate. The risks associated with them are often an unacceptable trade-off, for they require direct access to the arterial circulation. In addition, invasive methods are not suitable for repetitive measurements and normally cannot be performed outside a hospital. Furthermore, invasive methods are very demanding in terms of time consumption and the need for skilled personnel.

Impedance cardiography has been found to be one non-invasive method with the potential for monitoring the mechanical activity of the heart with virtually no risk. It can be conveniently handled by nursing and non-technical staff. It can usually tolerate moderate patient movement and can be left unattended for continuous and long-term monitoring.

U.S. Pat. No. 3,340,867, now RE 30,101, to Kubicek et al. discloses an impedance plethysmograph which employs four electrodes, two around the neck and two around the torso of a patient, to provide an impedance difference signal from the two center electrodes. The outermost pair of electrodes apply a small magnitude, high frequency alternating current to the patient while the inner pair of electrodes were used to sense voltage levels on the patient above and below the patient's heart. The impedances of the patient at each of the inner pair of electrodes could be determined from the sensed voltages and known applied currents.

According to Kubicek et al., stroke volume (SV) is related to impedance Z as follows:

$$SV = R(L/Z_o)^2 (VET)(dZ/dt_{min})$$

where R is blood resistivity, L is the distance between the inner voltage sensing electrodes, $Z_o$ is the mean thoracic impedance determined from the inner, voltage sensing electrodes, VET is the ventricular ejection time and $dZ/dt_{min}$ is the maximum negative slope change of the time-differentiated impedance signal, which is the time-differentiated difference between the impedances determined at the center two electrodes. The above equation is referred to as Kubicek's equation. Cardiac output per minute is stroke volume times heart rate in beats per minute.

The Kubicek equation is based upon a parallel column model of the thorax in which it is assumed:

(1) the thorax is a cylinder, consisting of two electrically conducting tissue paths, also of cylindrical form with uniform cross-sectional areas and homogenous conducting materials, the first path being the blood with a relatively low resistivity and the second path being all other tissues with relatively high resistivities;

(2) the relationship between the maximum impedance change and the stroke volume during the cardiac cycle is linear;

(3) impedance measurements of the individual specific tissue volumes are not very useful in developing the model (the parallel columns model relies on the intact thoracic measurements); and (4) at 100 kHz frequency, a physiologically safe frequency, the relative thoracic impedance changes are at a maximum, the effects of polarization are negligible, and the reactive component of impedance is small, especially when compared to the real component, so that the reactance could be ignored in determining impedance with only a small error.

Yet another model and equation for relating impedance and stroke volume has been proposed by Sramek. According to Sramek, stroke volume (SV) is related to impedance Z as follows:

$$SV = [(0.17H)^3/4.2] * [VET] * [dZ/dt_{min}/Z_o]$$

where H is the patient's height. The Sramek equation is based upon a frustoconical model of the thorax. The Sramek model illustrates some improvement and accuracy over the Kubicek model but its major assumptions are still similar to those of the Kubicek model.

Despite its advantages, impedance cardiography has not been well accepted by clinicians for three primary reasons:

(1) poor correlation of the methods and models with the results of the more accepted invasive techniques;

(2) still a relatively high dependance on skilled technical operators; and (3) still a discomfort to and/or disturbance of patients associated with the use and application of band electrodes.

It is believed that poor correlation, the primary reason, can be traced back to a single source, namely the continuing inability to relate impedance cardiography and its mathematical model directly to cardiac physiology.

The following are definitions and abbreviations of some of the terms used frequently herein:

Heart Rate (HR): the number of times the heart contracts each minute.

Ventricular Ejection Time (VET): the time interval of the opening and closing of aortic value during which there is movement of blood out of a ventricle.

Stroke Volume (SV): the volume of blood pumped out by a ventricle (in particular the left ventricle) with each contraction of the heart.

Cardiac Output (CO): the amount of blood pumped out of the heart into the systemic circulation each minute.

Ejection Fraction (EF): the ratio SV/EDV, which is the percentage of blood in a ventricle ejected with each contraction; it is directly related to the strength of the heart with <50% considered abnormal.

End Diastolic Volume (EDV): the volume of blood that fills the ventricle before ejection.

It would be desirable to determine heart rate more accurately than can be determined using the cardiogram threshold method currently employed.

It further would be desirable to provide non-invasive, cardiographic impedance monitoring to estimate stroke volumes, cardiac outputs and related cardiac function parameters which correlate more closely with the stroke volumes, cardiac outputs and the like determined by means of recognized, accepted invasive procedures, but which does not require of operators the technical skills required by current impedance cardiograph systems, and does minimize discomfort to the patient on which the system is used, thereby permitting relatively long-term monitoring of the patient's condition.

SUMMARY OF THE INVENTION

One aspect of the invention is a method of processing a time-derivative, thoracic impedance signal generated from a patient to identify events in the time-derivative signal associated with beats of the patient's heart. The method comprises the steps of generating a time-frequency distribution of data from the time-derivative impedance signal for a selected portion of the time-derivative impedance signal spanning a single heartbeat of the patient and identifying a time of occurrence of at least one event in the selected portion of the time-derivative signal from the time-frequency distribution.

Another aspect of the invention is a method of determining stroke volume of a patient's heart from thoracic impedance measurements. The method comprises the steps of applying a fluctuating excitation current to a patient through a first pair of electrodes located on opposing upper and lower sides of the patient's heart; generating from a second pair of electrodes located on opposing sides of the patient's heart between the first pair of electrodes a first signal related to impedance of the patient at the first electrode of the second pair and a second signal related to impedance of the patient at the second electrode of the second pair; identifying an impedance from each of the first and second signals occurring simultaneously with one heartbeat of the patient; and multiplying together the identified impedances of each of the first and second signals to estimate a cardiac parameter at least related to stroke volume of the patient's heart during the one heartbeat.

BRIEF DESCRIPTION OF THE DRAWINGS

In the drawings, like numerals are employed to indicate like elements throughout.

The foregoing summary as well as the following detailed description of the preferred embodiments of the invention will be better understood when read in conjunction with the appended drawings. For the purpose of illustrating the invention, there is shown on the drawings embodiments which are presently preferred. It should be understood, however, that the invention is not limited to the precise arrangements and instrumentality shown.

DETAILED DESCRIPTION OF THE PREFERRED EMBODIMENTS

Figure 1:
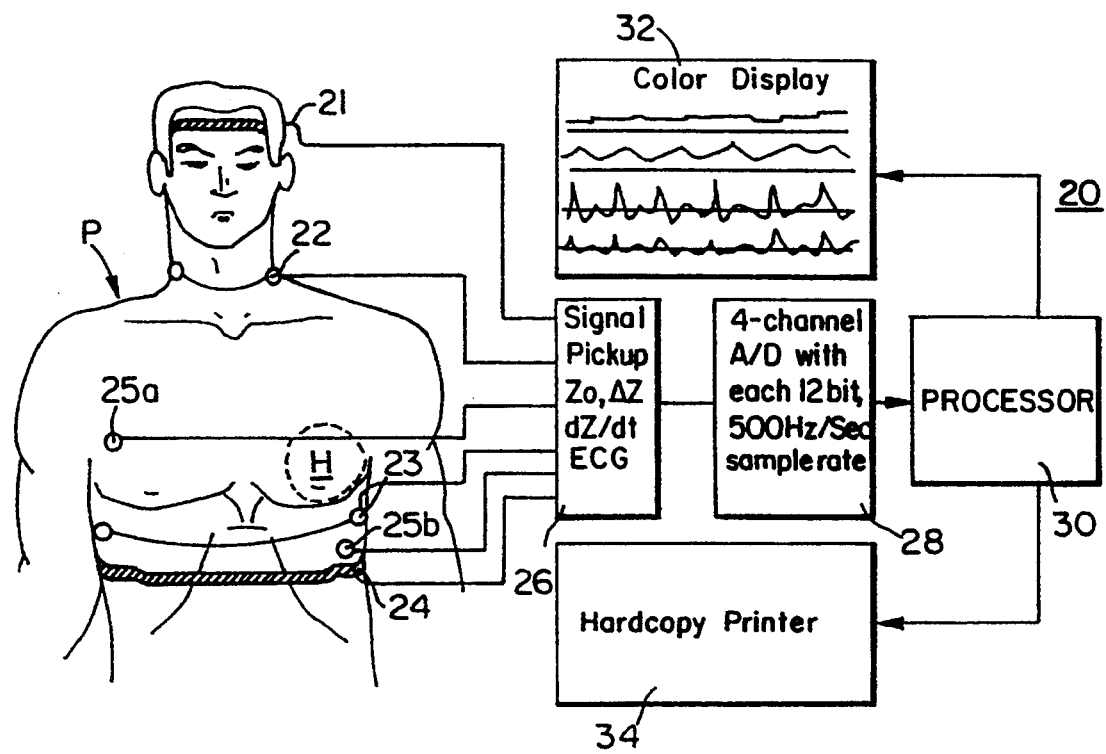
FIG. 1 depicts the cardiographic monitoring system of the present invention with the electrodes thereof applied to a patient P.

In the various figures like reference numerals are used to refer to like elements. There is shown diagramatically in FIG. 1 a preferred cardiographic impedance monitoring system according to the present invention, which is indicated generally at 20 and is coupled to a patient P for use. System 20 preferably includes a first, outer pair of electrodes 21 and 24, 21 being a strip electrode and 24 being a band electrode, and two pairs of parallel connected, spot-type skin electrodes, indicated generally at 22 and 23. The patient's heart is indicated diagrammatically, in phantom, at H. The first pair of electrodes 21 and 24 are applied to the patient's skin on opposite upper and lower sides of the heart H, preferably equally spaced from the heart. The pairs of parallel coupled spot electrodes 22 and 23 are applied to the patient on opposite upper and lower sides of the heart H respectively and between the first or outer pair of electrodes 21, 24. Each pair of electrodes 22 and 23 are preferably positioned on opposite lateral sides of the patient at uniform heights above and below the heart H. Again, electrode pairs 22, 23 are preferably equally spaced from or otherwise symmetrically positioned with respect to the heart H. A pair of conventional, electrocardiogram electrodes 25a and 25b are further provided.

Preferably, all five electrodes 21–25 are coupled through a signal pickup and preprocessor 26 and then through an analog to digital converter 28 to a data processor 30. Preferably a color video monitor 32 and an optional hard copy printer 34 are provided under the control of the processor 30. While a separate pair of electrocardiogram electrodes 25a and 25b is shown, it will be appreciated that the electrode pairs 22 and 23 might also be configured to generate an electrocardiogram signal by suitable processing of their signals. The outer pair of electrodes 21 and 24 are used to apply a fluctuating, preferably alternating current through the patient P between those electrodes 21 and 24 while electrode pairs 22 and 23 are provided to sense voltage levels on the patient P from which thoracic impedance is determined, as will be discussed.

The general advantages tetrapolar electrode configurations, such as that of system 20, have over bipolar electrode configurations are that the voltage sensing electrodes 22 and 23 are substantially free of skin impedance, can measure impedance with less electrode-interface artifact and offer the possibility of providing a more uniform current density distribution in the segment of interest in the patient.

There is a distortion in the current density distribution in patients in the vicinity of the current electrodes 21 and 24, known as the edge effect. In addition to edge effects, uniform current distribution is disturbed by the superposition of a relatively highly conductive sphere, namely the heart, and the relatively low conductivity of air in the lungs in the region between electrodes 22 and 23. The current distribution has been found to be more uniform in the central region between the electrodes 21 and 24 the more widely spaced those electrodes are. In addition, it has been found that the positions of the current electrodes 21 and 24 relative to those of the voltage detecting electrodes 22 and 23 are further important to ensure uniform current distribution. It has been found that if the distances between adjoining pairs of the electrodes 21 and 22, and 23 and 24 are sufficiently great, at least about 3 cm and, preferably, about 4 cm or more, the edge effect is essentially minimized and the impedance measurement becomes stable.

The upper current electrode 21 is preferably applied to the patient's forehead while the upper voltage sensing current and pick-up electrodes 22 are applied to the patient's neck. This configuration has several advantages over previous systems employing neck current and pickup electrodes. It is a simple configuration for the technician to remember while assuring that the upper two electrodes 21 and 22 are sufficiently separate to avoid edge effects. The further spacing of the upper current electrode 21 from the heart provides a more uniformly parallel current distribution and equal potential lines through the patient, particularly in the area between the measuring electrodes 22 and 23. In addition, this arrangement minimizes the problem of attempting to locate all upper electrodes 21 and 22 on the patient's neck where catheters and bandages are often encountered. The forehead is usually untouched by medical devices. All four electrodes 21–24 are preferably mounted to the patient in parallel planes to optimize the uniformity of the current distribution and the location of the sensing electrodes 22 and 23 along the equal potential lines.

Band electrodes have been found to provide the most parallel current lines and equal potential distributions through the patient and therefore should, at least theoretically, give the best results. There are several disadvantages to band electrodes. They may be difficult or impossible to apply to patients with extensive chest wounds because of the presence of dressings, tubes, etc. They require relatively long polarization time to stabilize before measurements can be taken and, therefore, may not be useable in emergency situations. They are more sensitive to motion artifact due to the large area of contact of the electrode. Lastly, they are generally more uncomfortable for patients when used for long-term monitoring. The advantages and disadvantages of spot electrodes are just the reverse of those of the band electrodes.

The correlation between the results of using an all band electrode configuration and the mixed band and spot electrode configuration shown in FIG. 1 were distinctly higher (correlation coefficient equal to about 0.95) than the correlation between an all band and an all spot electrode configurations (correlation coefficient equal to about 0.75). The combined band and spot electrode configuration shown in FIG. 1 appears to have all the advantages of each type with almost no disadvantages of either. In particular, the mixed electrode system supplies parallel, iso-current lines and parallel equal potential lines generally perpendicular to the iso-current lines. The system is easy to apply to patients, even with extensive chest wounds, dressing, tubes or the like on the chest. It has relatively short polarization time and thus can be used in emergency situations. It is less sensitive to motion artifact due to the small area of contact provided by spot electrode pairs 22 and 23 which provide the impedance signal. The spot electrodes 22 and 23 are also more comfortable to the patient.

The signal pick-up and preprocessor 26 is preferably a Minnesota Impedance Cardiograph (MIC) Model 304B, supplied by Sorocom, Inc., of Minn. The MIC 304B provides a high frequency (approximately 100 kHz), low amplitude (4 mA RMS) alternating current at pick-ups provided for the electrodes 21 and 24. Pick-ups are also provided for the parallel coupled voltage sensing electrode pairs (22) and (23) and for the EKG electrodes 25a, 25b.

The preferred MIC preprocessor generates and outputs four analog signals: the mean thoracic impedance signal ($Z_o$), the change in thoracic impedance signal (delta Z or $\Delta Z$), the time-derivative impedance signal (dZ/dt) and the electrocardiogram signal (EKG). The mean thoracic impedance signal, $Z_o$, is the impedance difference sensed between electrodes 22 and 23. The change in thoracic impedance signal, delta Z, is an amplification of the original $Z_o$ signal from which the DC component has been removed. The time-derivative impedance signal, dZ/dt, is the time derivative of the amplified delta Z signal. The EKG signal is conventional. The four signals are shown diagrammatically on monitor 32 in FIG. 1 while expanded versions of the dZ/dt and EKG signals are shown in FIGS. 2a and 2b, respectively.

Figure 2A:
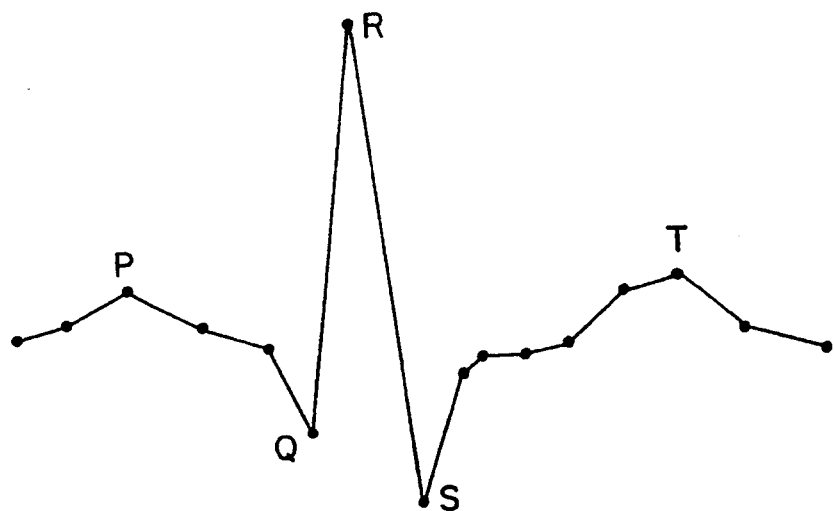
FIG. 2a depicts a portion of an exemplary EKG signal spanning a single heartbeat.
Figure 2B:
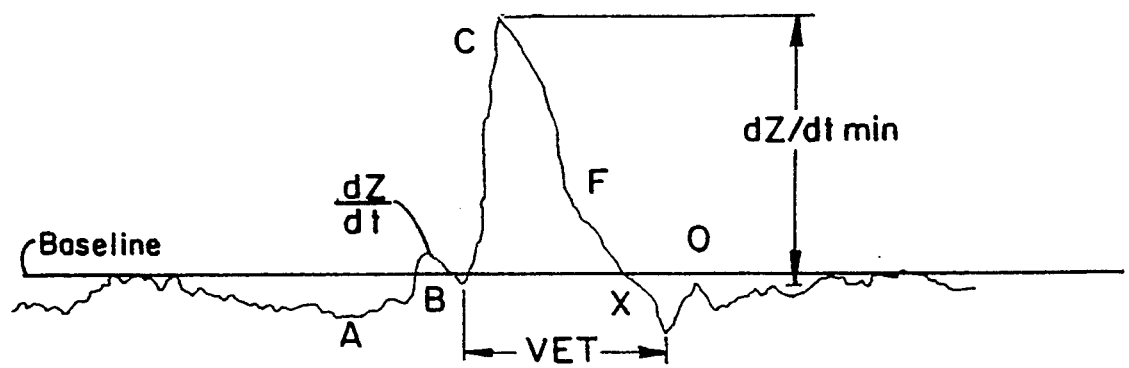
FIG. 2b depicts a portion of an exemplary inverted dZ/dt signal spanning a single heartbeat.
Figure 2C:
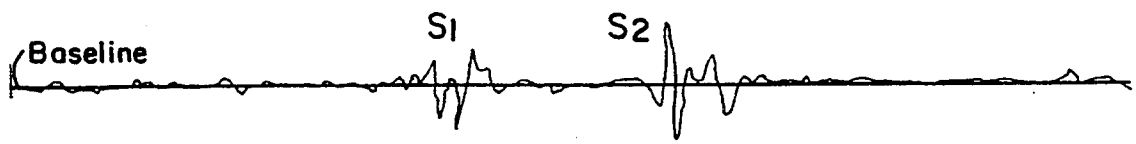
FIG. 2c depicts a portion of an exemplary phonocardiogram signal spanning the same heartbeat shown in the dZ/dt signal.

FIG. 2a depicts a portion of an exemplary EKG signal while FIG. 2b depicts a portion of an exemplary inverted dZ/dt signal. FIG. 2c depicts a portion of an exemplary phonocardiogram signal corresponding to the dZ/dt signal. The dZ/dt signal is conventionally inverted so that its maximum slopes will appear positive, thereby enabling the clinician to observe the cardiac event in a more familiar manner.

Cardiac events appear in the impedance and EKG signals as perturbations or "waves". EKG waves related to each heartbeat are also noted on the EKG signal of FIG. 2a at P, Q, R, S and T. The waves which are related to a single heartbeat and which appear in the dZ/dt signal are indicated in FIG. 2b at A, B, C, F, X and O. Heart sounds (S1 and S2) associated with the compression and relaxation, respectively, of the heart during a single beat, are overlaid in the dZ/dt signal of FIG. 2b. In many cases, however, the identification of individual waves in either signal is not so apparent.

The four analog signals from the preprocessor 26 are passed to the analog digital converter 28. Preferably, the A/D converter 28 is configured for differential conversion at a sampling rate of 500 Hz for each of the four analog signals with a twelve bit resolution in offset binary format. The analog to digital converter may be, for example, a Data Translation Model DT 2811/PGH.

The four digitized signals are preferably passed into an allocated memory such as a hard disk or RAMDISK in or associated with the processor 30 and stored in binary format for subsequent processing. The processor 30 preferably also formats the binary data signals for real time or essentially real time display on the video monitor 32. At least the dZ/dt and the EKG signals from preprocessor 26 are displayed for the clinician on the monitor 32 but the $Z_o$ signal and the delta Z signal are also preferably simultaneously displayed for the clinician who can check the validity of the various signals as they are being acquired. Preferably, system 20 processes the impedance and EKG signal data to determine at least the heart rate (HR) and the cardiac output (CO) of the patient in at least near real time and preferably displays those values as well. These and other values determined by the process may be printed out on the hard printer 34.

Figure 3A:
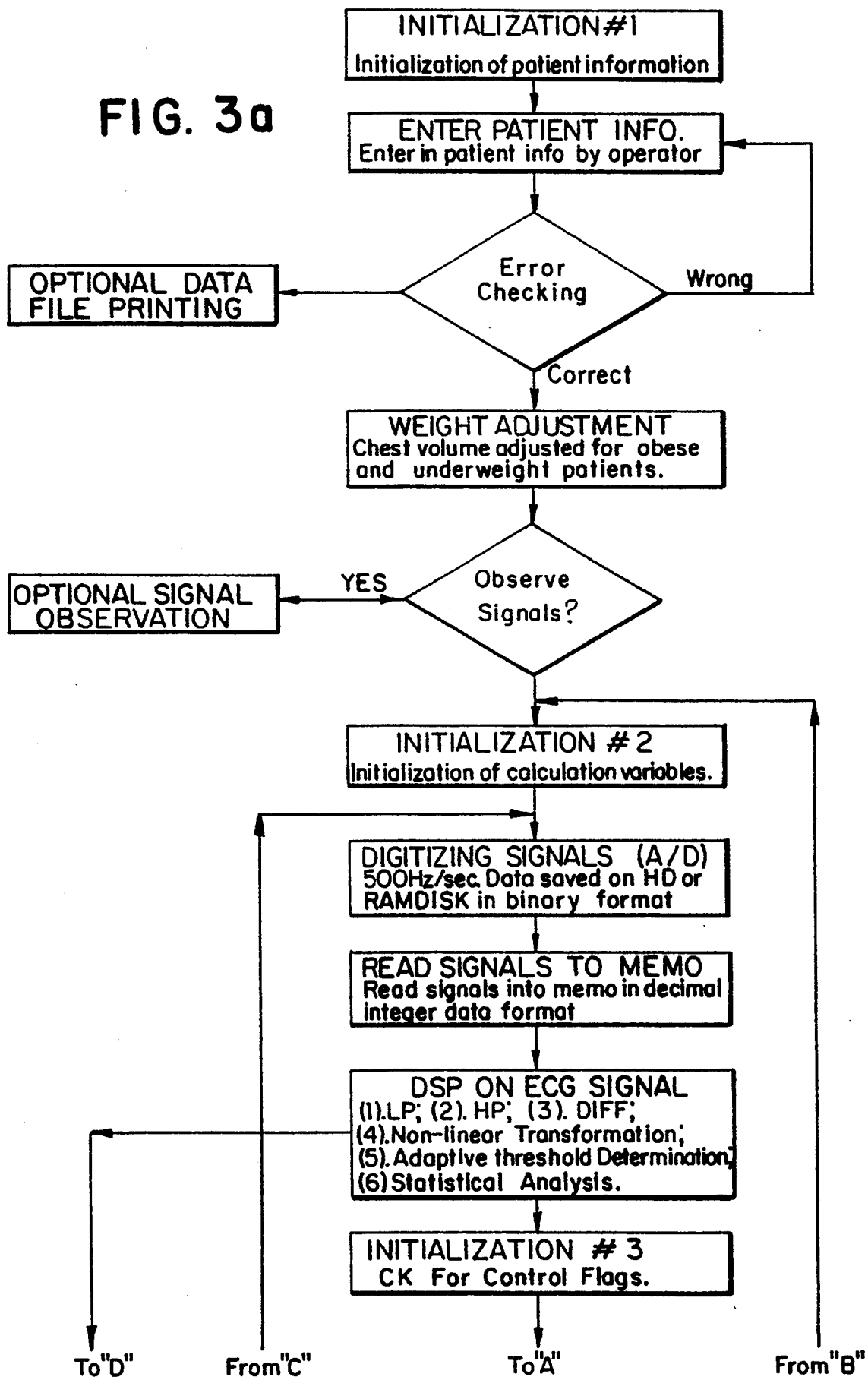
FIGS. 3a–3b depict in block diagram form, the steps followed by the processor of the system in determining the various cardiac parameters identified and calculated by the system.
Figure 3B:
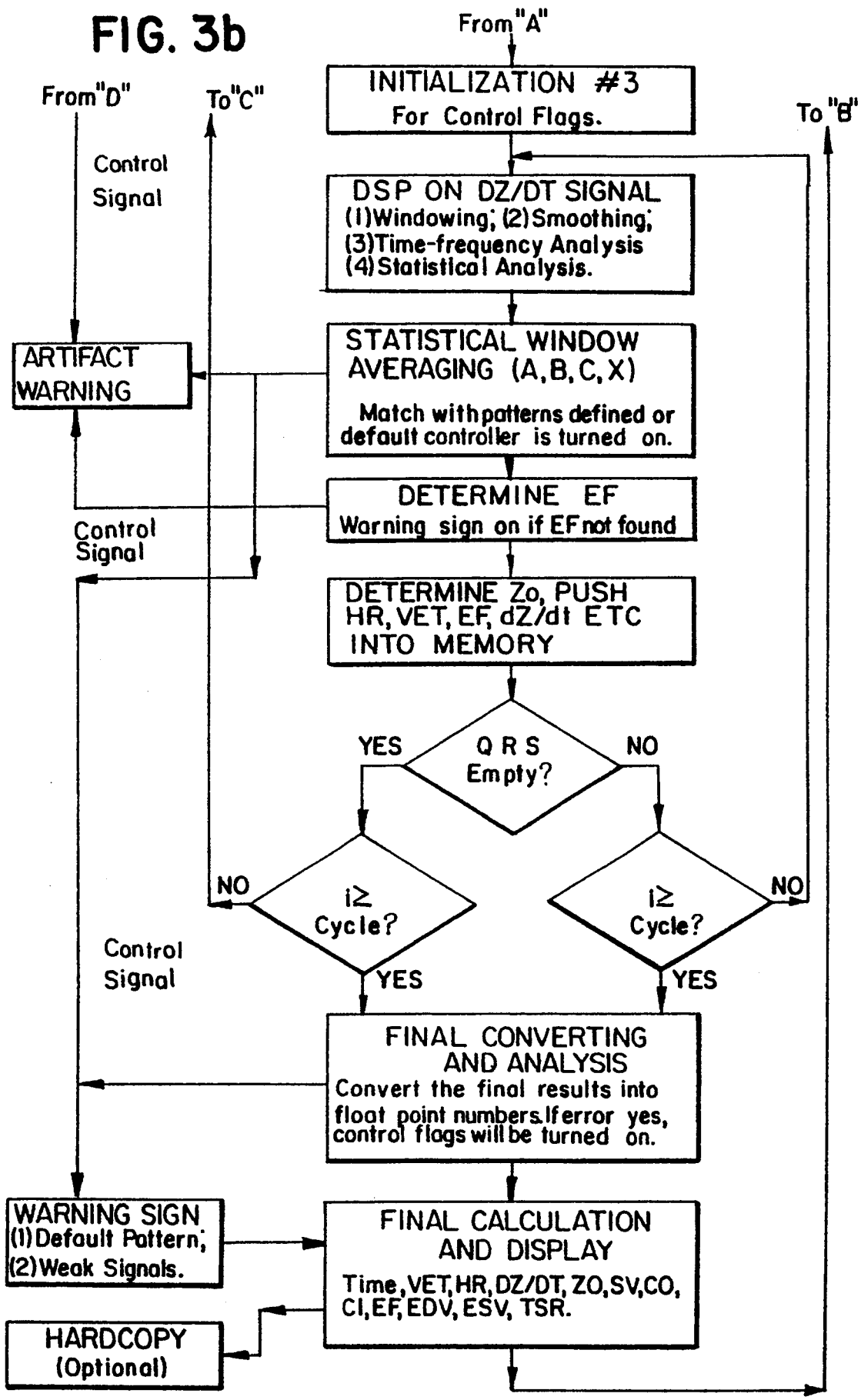

FIGS. 3a–3b depicts in block diagram form, the operational steps of the processor 30 in determining heart rate, cardiac output and optionally a variety of other parameters reflecting cardiac performance begins the generation of data. Preferably, the system 20 is configured to be operable in a predata signal processing mode in which the preprocessor 26 and ADC 28 operate to pass binary data signals to the processor 30 which formats the signals for real-time or essentially real-time display on monitor 32. After the clinician has verified successful signal gathering and digitization through the display, the data signal processing for cardiac parameter determinations are begun. Preferably the processor 30 will initialize the necessary calculation variables and begin storing the binary EKG and impedance signal data in a hard disk or RAMDISK in the binary format for subsequent processing.

Initial data processing includes converting the stored binary impedance and EKG signal data into decimal integer format and reading the decimal format data into a working memory area of the processor 30 in predetermined time period blocks for processing. The EKG signal data is first processed by low-pass (LP) and high-pass (HP) filtering, then differentiated and thereafter non-linearly scaled or transformed. The filtered, differentiated, scaled EKG data is then further adaptively processed to detect the R wave peaks, which are used to identify the cardiac cycles of the heartbeat, and to validate the detected peaks. If valid, the processor 30 stores the time of occurrence of each validated peak as the peak of an R wave in the EKG signal block.

In particular, preferably each consecutive five second block of the processed EKG signal data is searched for its maximum peak. The maximum peak is multiplied by a predetermined fractional value, preferably 0.5, to generate a tentative threshold. The block of data is searched to identify peaks that are greater than or equal to this threshold, with each consecutive pair of peaks being separated by a predetermined time interval, preferably in the range of 0.28 to 4.5 seconds. The coefficient of variation ("C.V."=Standard Deviation/Mean) of the peak time intervals is determined and compared to a predetermined ratio, preferably 0.3. If the determined C.V. is less than or equal to this predetermined ratio (0.3), the identified peaks are accepted as the R wave peaks. If the determined C.V. is larger than this ratio (0.3), and if the number of intervals that are less than the mean is more than the number of intervals that are greater than the mean, then the tentative threshold is reset by multiplying the maximum EKG value by a smaller predetermined fractional value, preferably 0.4. If the reverse is true, i.e., if the determined C.V. is larger than the predetermined ratio (0.3) and the number of intervals that are less than the mean is less than the number of intervals greater than the mean, then the tentative threshold is reset by multiplying the largest EKG value by a larger predetermined fractional value, preferably 0.6. The process is repeated to determine the C.V. of the newly identified intervals, as was done with the originally tentative threshold. If the determined C.V. still exceeds 0.3, the data block is discarded and the next block of processed EKG signal data is examined.

After checking for control flags that may have been generated during EKG signal block processing for the proscribed C.V. value, the processor 30 processes the data from the impedance signals, particularly the dZ/dt signal. Briefly, the R wave peaks identified from the EKG signal are used to "window" or define blocks of the dZ/dt data spanning a single heartbeat for processing. A portion of the time-derivative impedance signal dZ/dt is selected to span one heartbeat of the patient. The time-derivative impedance signal preferably is smoothed by low-pass and high-pass filtering and a time-frequency distribution of the filtered data from the windowed portion of the time-derivative impedance signal is generated in a manner to be described. Preferably, the time-frequency distribution is thereafter analyzed, preferably in conjunction with the time-derivative impedance signal, to identify from the time-frequency distribution a time or times of occurrence of at least one, and preferably two, cardiac events in the selected portion of the time-derivative signal. If the processor 30 is unable to identify the waves being sought, an artifact warning control signal is generated to set a control flag. Otherwise, the pertinent parameters from the various impedance signals, as well as related values derived from those signals including, but not limited to, the mean impedance $Z_o$ at the peak of the heartbeat contraction, $dZ/dt_{min}$, heart rate (HR), ventricular ejection time (VET), and all other parameters which may be identified or determined are moved into memory for storage. The process is repeated for each heartbeat identified in the interval of the processed EKG signal, which was originally selected to include the several consecutive seconds of data with several consecutive heartbeats of the patient. When the various parameters have been determined for each heartbeat of the interval (QRS Empty), the processor sets control flags for any errors noted and performs any remaining calculations. The processor then converts the identified and determined values into floating point numbers. Lastly, the processor preferably displays some or all of the identified and determined values on the monitor 30 and prints them on the hard copier 32, if desired.

A distinct advantage possessed by the present system over prior known systems is the filtering method employed for processing the digitized EKG and impedance signals.

Preferably, all filtering is digitally performed by processor 30 and the filters used are designed to employ only integer coefficients. This allows the filters to operate in near real-time on a relatively simple microprocessor such as an IBM ® or IBM ® compatible personal computer, which is also employed to perform the remaining processing steps.

The all-integer filter designs of the present invention are both simple to program and fast to execute. They have proven to be more than capable of handling at relatively high speed the data filtering required by the present system. They utilize a high-level, C language without the need for assembly language programming or a co-processor. The filters of the invention use only a relatively small number of multiplier and additional components, all with integer coefficients. A brief derivation of the filters follows.

The usual auto-regressive moving average (ARMA) system can be represented by the equation:

$$y[n] = a_1 y[n-1] + \ldots + a_m y[n-m] + b_0 x[n] + \ldots + b_k x[n-k]$$

For a low-pass filter, consider a special case of the moving average (MA) system:

$$y[n] = x[n] - x[n-k]$$

Its transfer function is:

$$H(z) = 1 - z^{-k}$$

where $z = e^{sT}$ and T is the sample interval.

The k zeros in the z-plane are the roots of:

$$1 - z^{-k} = 0$$

Consider the case k=12 for the z plane represented by a real abscissa (X axis) and an imaginary ordinate (Y axis), i.e. $Z(x,y) = Z(real, imaginary)$. If a zero at $z=(1,0)$ of the unit circle for the real and imaginary values in the z-plane, respectively, is cancelled, then the following low-pass filter transfer function is obtained:

$$H(z) = (1 - z^{-k})/(1 - z^{-1})$$

This transfer function yields the recursive relation:

$$y[n] = y[n-1] + x[n] - x[n-k]$$

To improve the side lobes ($-14$ dB), second or third order zeros and poles may be taken:

$$H(z) = (1 - z^{-k})^2/(1 - z^{-1})^2, \text{ or}$$

$$H(z) = (1 - z^{-k})^3/(1 - z^{-1})^3$$

which greatly improves the sidelobes ($-27$ dB, $-42$ dB). The recursive equation becomes:

$$y[n] = 2y[n-1] - y[n-2] + x[n] - 2x[n-k] + x[n-2k].$$

The total order of this system has become 2k (or 3k). For k=12, the total system needs to preserve only 24 (or 36) data points.

By moving the cancelling pole $z=(1,0)$ to $z=(-1,0)$, a high-pass filter is obtained with the following transfer function:

$$H(z) = (1 - z^{-k})^2/(1 + z^{-1})^2$$

and the following recursive equation:

$$y[n] = -2y[n-1] - y[n-2] + x[n] - 2x[n-k] + x[n-2k]$$

Cancelling the zeros on the unit circle at any angle q in the z-plane other than $z=(1,0)$ and $z=(-1,0)$ will give a band pass filter. However, if only integer coefficients are desired, some restrictions should apply since any pair of those zeros will result in the cosine function:

$$1 - \frac{2\cos q}{z} + \frac{1}{z^2}$$

Accordingly, angle q must be 60°, 90° and 120°, correspondingly located at 1/6T, 1/4T and 1/3T. The bandwidth can then be managed by the integer k and T.

An example of a band pass filter with a center frequency $f = 1/4T$ and nominal bandwidth $NB = 1/6T$, would include the following transfer function and recursive equation:

$$H(z) = (1 - z^{-12})^2/(1 + z^{-2})^2 \text{ and}$$

$$y[n] = 2y[n-2] - y[n-4] + x[n] - 2x[n-12] + x[n-24]$$

Consider an ideal, continuous time differentiator and its respective frequency response:

$$y(t) = \frac{d}{dt}[x(t)] \text{ and}$$

$$H(j\Omega) = j\Omega$$

Since the input signal is restricted to be bandlimited, it would be satisfactory if the continuous response could be:

$$H_{eff}(f^\Omega) = f^\Omega, \; |\Omega| < \pi/T,$$
$$= 0, \; |\Omega| > \pi/T$$

The corresponding discrete-time differentiator has the following frequency response and is periodic with period $2\pi$:

$$H(e^{j\omega}) = j\omega/T, \; |\omega| < \pi$$

It can be shown that the corresponding impulse response of this discrete frequency response can be represented as:

$$h[n] = [n\pi\cos(n\pi) + \sin(n\pi)]/n^2\pi T - \infty < n < \infty$$

which is zero for n=0 and as follows for n not equal to zero:

$$h[n] = [\cos(n\pi)]/nT.$$

For example, a 6-point differentiator would be represented as:

$$y[n] = (x[n+3]/3 - x[n+2]/2 + x[n+1] - x[n-1] + x[n-2]/2 - x[n-3])/T.$$

A preferred, low-pass auto-regressive moving average filter is employed having a nominal bandwidth = ±33.3 Hz, Sidelobes = −27 dB, K=15, T=500 Hz/sec, Delay=15T, Gain=225, having the following transfer function and recursive formula:

$$H(z) = (1 - 2z^{-15} + z^{-30})/(1 - 2z^{-1} + z^{-2})$$

$$y[n] = 2y[n-1] - y[n-2] + x[n] - 2x[n-15] + x[n-30]$$

Figure 4:
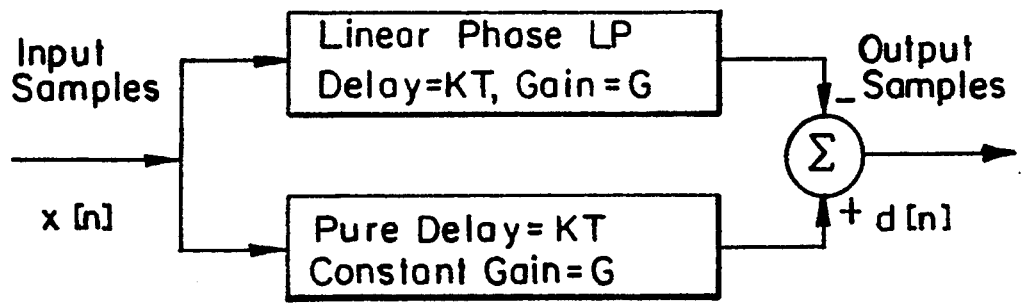
FIG. 4 depicts schematically a linear phase delay filter for combined low-pass, high-pass filtering.

A preferred high-pass ARMA filter is employed in the system having a bandpass = ±5 Hz, and sidelobes = −14 dB. Because of the T restriction for the specific high-pass filter, a low-pass filter is designed first and then subtracted by means of a linear phase delay filter, as shown in FIG. 4. The low-pass filter is represented by the following transfer function and recursive formula, respectively:

$$HL(z) = (1 - z^{-100})/(1 - z^{-1})$$

$$y[n] = y[n-1] + x[n] - x[n-100]$$

where K=100, T=500 Hz/sec, Delay=100T, and Gain=100.

The preferred delay filter used in FIG. 4 is represented by the recursive formula:

$$d[n] = 100x[n-100] - y[n]$$

where d[n] represents the high-pass filter output samples.

A preferred moving average (MA) differentiator used by the system 20 for differentiating the EKG signal data after low-pass/high-pass filtering has a linear slope bandwidth = ±35 Hz and the following transfer function and recursive formula:

$$H(z) = -z^{-4} - 2z^{-2} + 2z^{+2} + z^{+4}$$

$$y[n] = -x[n-4] - 2x[n-2] + 2x[n+2] + x[n+4]$$

where K=4, T=500 Hz/sec, and Delay=4T.

Figure 5:
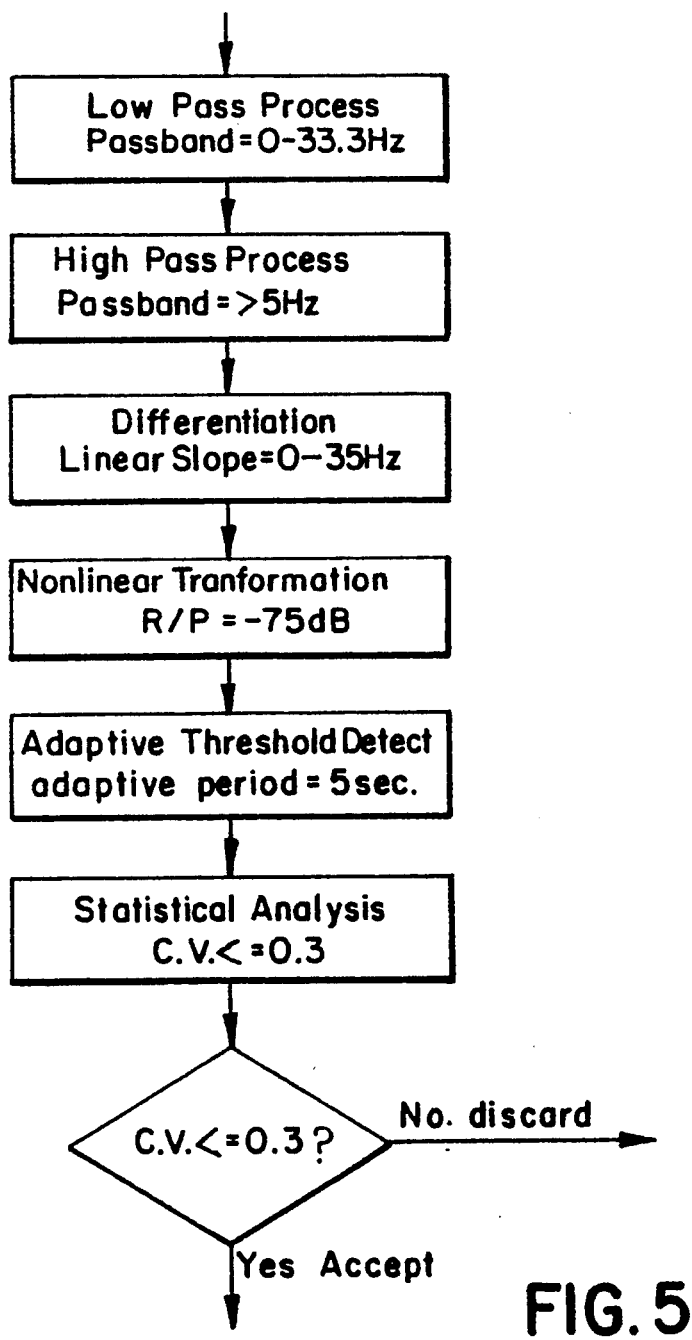
FIG. 5 depicts in block diagram form the detailed steps of the EKG signal processing.

FIG. 5 depicts diagrammatically in block diagram form and greater detail, the sequence of steps preferably followed by the processor 30 to process the digitized EKG data and to identify the R wave pulses. The EKG data stored in binary form is converted into digital data in blocks containing the continuous EKG signal data for a predetermined period of time. The blocks are selected to include several consecutive seconds of data from the EKG signal for several consecutive heartbeats of the patient. Five second long blocks of EKG signal data are presently preferred as such blocks are sufficiently long to permit the elimination by filtering of artifacts which might be caused by arrhythmia or patient movement and yet are sufficiently short that they still permit the various digital filters of the system to handle heart rates of between about and 214 beats per minute.

Processor 30 preferably first converts the block of binary data into digital format values. It then low-pass filters the decimal format data, high-pass filters the low-pass filtered data, and applies the twice-filtered data to the previously described differentiator or derivative filter. The filtered, differentiated data is then non-linearly scaled, preferably by squaring for convenience, although raising the data by any power greater than one will provide non-linear scaling. The preferred low-pass ARMA filter has a nominal bandwidth equal to ±33.3 Hz to remove the components of the EKG signal which may be provided by external electrical interference, specifically 60 Hz AC line and other higher frequency interferences. The preferred high-pass ARMA filter has a band pass equal to ±5 Hz to eliminate unwanted low-frequency components representing slow motion artifacts such as respiration and other physical patient movements and such anomalies as arrhythmia. The preferred MA differentiator has a linear low bandwidth equal to ±35 Hz to extract and emphasize data concerning the slope change of the EKG signal. The non-linear transformation is preferably significantly great to provide an R/P equal to −75 dB where R and P stand for the amplitudes of the R and P waves, respectively, of the EKG signal associated with each heartbeat. Squaring has proved adequate. The filtered, differentiated, non-linearly scaled five second block of EKG signal data will include a number of peak values, the greatest of which will correspond to the separate R wave peaks of the original EKG signal.

According to an important aspect of the present invention, an adaptive threshold is set for each multisecond block of EKG data. This is done by identifying the magnitude of the maximum amplitude value of the filtered, differentiated, non-linearly scaled data of the block, setting a predetermined fraction of that magnitude, for example, 0.5, as a tentative threshold. All data points in the block of filtered, differentiated, non-linearly scaled data having an amplitude at least as great and preferably greater than that predetermined fractional threshold are identified and processed to determine the average of the identified amplitudes and a standard deviation of the identified amplitudes. The processor thereafter determines the coefficient of variation (CV) of the identified amplitudes, where CV = standard deviation/mean. If the coefficient of variation exceeds a predetermined value, preferably 0.3, none of the identified amplitudes are accepted or validated and that block of EKG data is preferably discarded. If the coefficient of variation of the amplitudes is equal to or less than the predetermined fraction, the EKG data is further processed.

A bi-level timing signal preferably is generated from the times of occurrence of those identified amplitudes remaining after the foregoing processing and is output as a pulsed, heart rate signal, which can be displayed on the monitor 30 and/or recorded.

Testing of this process on a large number of patients, including some with pacemakers and some exercising on a stationary bicycle, was found to provide a correct R wave detection rate for more than ninety-five percent of the EKG signals where a coefficient of variation of 0.3 was employed.

Next, the processor 30 preferably processes a block of the impedance signal data overlapping the selected block of processed EKG data to identify cardiac events reflected in the impedance signals from which the Ventricular Ejection Times (VET) may be estimated.

The VET plays an important role in impedance cardiography since it represents the time period between the opening and closing of the aortic valves during the systole-diastole cycle of the heart. It has not been clear how the VET should be defined with respect to the time-derivative impedance signal dZ/dt. Several alternative definitions have been proposed including:

(1) the horizontal distance (time) between two zero crossing points of the dZ/dt signal;
(2) the distance from a first zero crossing of the dZ/dt signal, before the occurrence of the "X" wave, to the "x" wave of the dZ/dt signal;
(3) the distance between the 0.15* $dZ/dt_{min}$ point and the X wave of the dZ/dt signal;
(4) the distance between the A and X waves of the dZ/dt signal; and
(5) the distance between the B and X waves of the dZ/dt signal.

The latter two definitions are baseline independent. The last of these definitions is presently preferred because the B and X waves are considered to represent the onset points for opening and closing of the valves and thus, physiologically correspond most closely to the end points of the theoretical interval being determined. However, this last definition is perhaps the definition least used because it is the most difficult one to detect. The B and X points often, if not usually, disappear into the noise of the basic dZ/dt signal.

According to another important aspect of the invention, a time-frequency distribution analysis is generated to extract detailed information on the transient behavior of the non-stationary dZ/dt signal. This leads to the concept of a mixed time-frequency signal representation.

A general class of time-frequency distributions was introduced by Cohen and have the following form:

$$C_f(t,\omega;\phi) = \frac{1}{2\pi} \int_{-\infty}^{\infty} \int_{-\infty}^{\infty} \int_{-\infty}^{\infty} e^{j(\xi t - \tau\omega - \xi u)} \phi(\xi,\tau) \times f\left(u + \frac{\tau}{2}\right) f^*\left(u - \frac{\tau}{2}\right) du d\tau d\xi$$

where f(u) is the time signal, f*(u) is its complex conjugate, and $\phi$ is a kernel function which represents the particular distribution function selected. Several distributions have been derived from this Cohen distribution including: the Rihaczek distribution, the Page distribution, the Levin distribution, the Wigner distribution, the cumulative decay or attack spectrum and the Spectrogram distribution.

Preferably, a Spectrogram time-frequency distribution of the digitized dZ/dt signal is used by the processor 30. The Spectrogram distribution, which is sometimes called the time-dependent Fast Fourier Transform (FFT), is defined generally as:

$$X[n,\omega] = \sum_{m=-\infty}^{\infty} f[n+m]w[m]e^{-j\omega m}$$

where f[n] is the digitized dZ/dt time signal data and w[n] is a window function. Window functions particularly useful with Fourier transforms include rectangular, Bartlett (triangular), Hanning, Hamming, and Blackman. Preferably, a Hamming window function is used having the following equation:

$$w[n] = 0.54 - 0.46\cos(2\pi n/L), \quad 0 \leq n \leq L$$
$$= 0, \quad \text{otherwise.}$$

Variable n=0,1, . . . ,L−1 and corresponds to data points of the digitized dZ/dt signal; L is the total number of data points (n) in each FFT process.

When multiplied by a window function, the one-dimensional discrete signal f[n] (i.e. the digitized dZ/dt signal) is converted into a two-dimensional function with a time variable and a frequency variable. Its time-dependent Fourier transform can also be interpreted as the Fourier transform of f[n+m] as viewed through the window w[m]. The window has a stationary origin and as n changes, the signal slides past the window so that, at each value of n, a different portion of the signal is viewed.

A major advantage of time-frequency analysis utilizing a Spectrogram distribution is that for the purposes of the present system 20, such an analysis is possible with the computational power of the preferred microprocessor 30. The corresponding disadvantage of a Spectrogram analysis is that there is a trade off between time and frequency resolution. An underlying assumption in using a window is that the spectral characteristics of the signal being viewed can be considered reasonably stationary over the window's duration. The faster the spectral characteristics of the signal change, the shorter the window duration should be. A shorter window length provides a higher resolution in time changes. However, the shorter the length of the window duration, the lower the frequency resolution will be. This is because the resolution of narrowband components will be sacrificed as window duration decreases. To increase frequency resolution, the window length must be increased.

The primary frequency components of the power spectrum density of typical thoracic impedance signals are found scattered approximately within the range of 2–40 Hz. However, the present system and method is preferably interested only in the contribution within the range of approximately 30–55 Hz, corresponding most closely to the frequency of opening and closing of the aortic valve.

Figure 7:
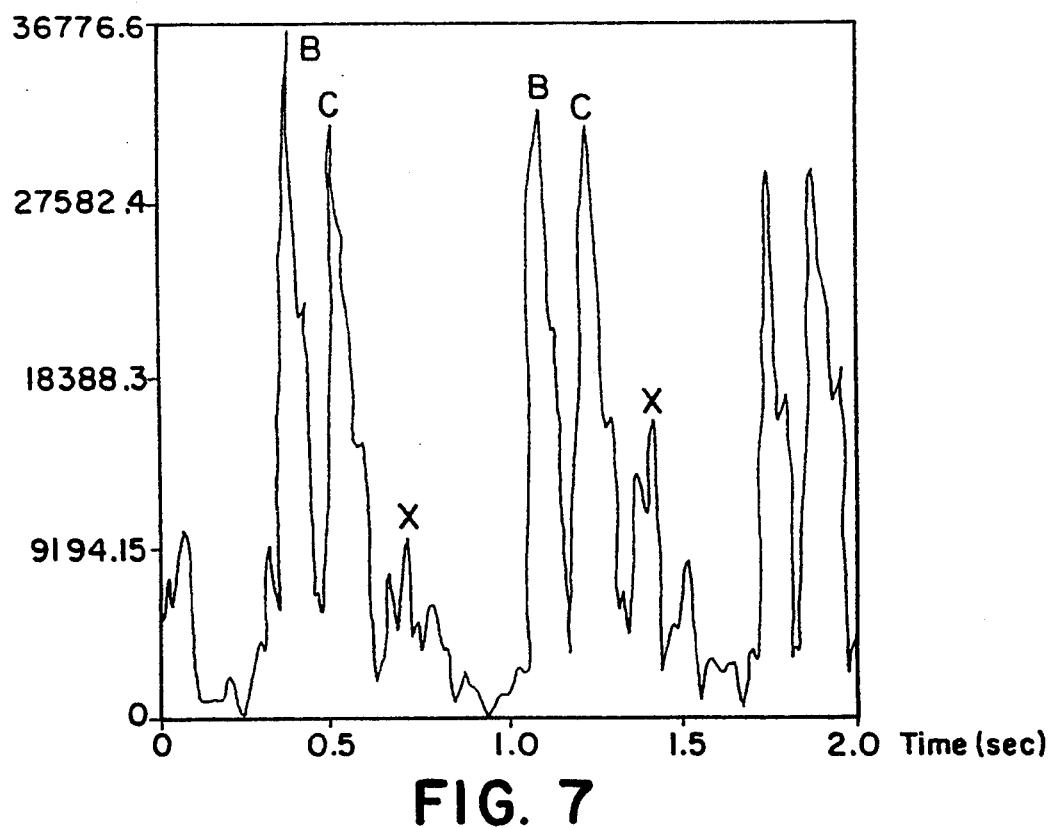
FIG. 7 depicts an exemplary local power distribution for a frequency range of interest derived from a Spectrogram time-frequency distribution of the time differential impedance signal.

The Spectrogram distribution is preferably calculated for each R—R interval. The Spectrogram distribution data is used to derive a function S(k), an example of which is depicted in FIG. 7, which indicates the amplitude (i.e. power) contributions to the time derivative impedance signal (dZ/dt) of the frequencies in interest (about 30 Hz to 55 Hz), within the limits of the digital computations provided by the preferred embodiment system. To be certain that the Spectrogram distribution captures the pertinent frequency data in the dZ/dt signal associated with each heartbeat, Fast Fourier Transforms used to generate the Spectrogram distribution components are preferably determined for each heartbeat beginning at a point in time before the occurrence of the heartbeat. Preferably, the time period over which the Spectrogram distribution is calculated begins before the R wave peak $R_i$ of the heartbeat in question, preferably about twenty percent of the time interval between the heartbeat in question ($R_i$) and the next heartbeat ($R_{i+1}$). For simplicity, reference will hereafter be made to R—R intervals but it will be understood where it is not stated that these intervals are shifted slightly backwards in time for the Spectrogram distribution computations. Preferably, the heartbeat times and intervals (R—R intervals) are defined by the previously derived R peaks and/or heart rate signal. The FFT is preferably calculated with the low-pass/high-pass filtered (smoothed) dZ/dt(n) data.

Figure 6:
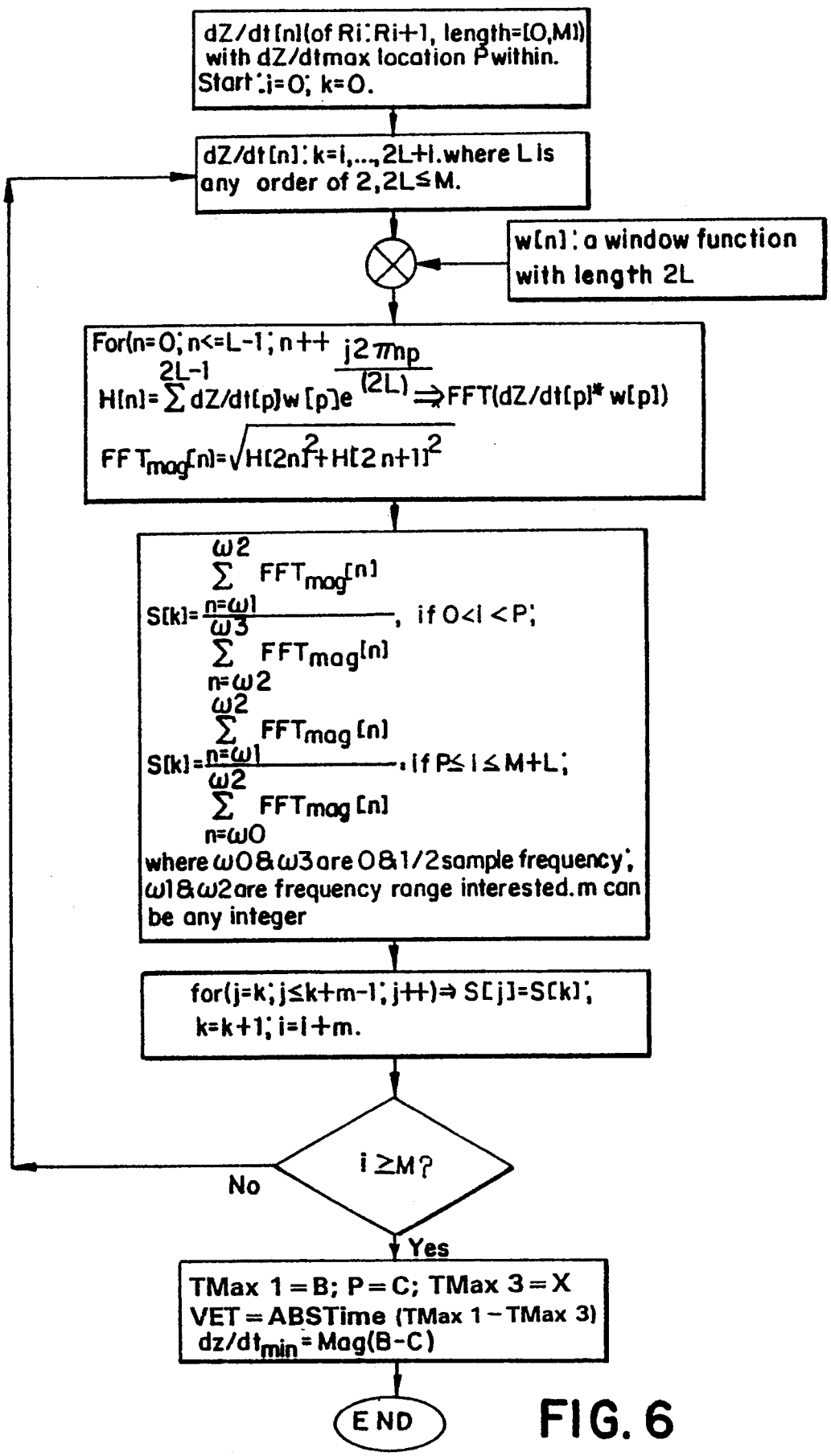
FIG. 6 depicts in block diagram form the detailed steps of the time differential thoracic impedance signal processing.

The following variable names have been employed in FIG. 6:

$R_i$: The discrete time location of a particular R spike of the EKG signal.

$R_{i+1}$: The discrete time location of another R spike immediately after $R_i$ of the same EKG signal.

M: The number of dZ/dt sample points between the $R_i$ and $R_{i+1}$ locations (M=$R_{i+1}$ − $R_i$) and is a varying number.

D: The number of points the $R_i$ and $R_{i+1}$ locations are shifted backwards in time.

B: Location of B wave peak of the dZ/dt signal in the $R_i$ to $R_{i+1}$ interval.

X: Location of X wave peak of the dZ/dt signal in the $R_i$ to $R_{i+1}$ interval.

P: Location of dZ/dt$_{max}$ within the $R_i$ to $R_{i+1}$ interval.

w[n]: A window function of data points "n".

H[n]: Fourier transform value for a frequency value that corresponds to n.

L: Half the length of an FFT process.

m: The number of points or STEP, that a 2*L duration moves ahead (to the right) in the time domain within the $R_i$ to $R_{i+1}$ cycle. Note that m<<2*L and preferably equals 1.

S: Spectrogram derived function.

The signals are processed R—R cycle by R—R cycle. Again, each R—R cycle is purposely shifted backwards early in time by D points. D is preferably twenty percent of the total number of $R_{i+1}$ − $R_i$ data or sample points. This is to assure that the A and B points of the heartbeat associated with $R_i$ are located inside the process cycle. The preferred sample rate is 500 Hz per channel (i.e. Zo,$\Delta$Z,dZ/dt and EKG).

Physiologically, within every process cycle $R_i$ to $R_{i+1}$, there is a peak dZ/dt value. This peak value is dZ/dt$_{min}$ when referring to the time derivative of the impedance signal and dZ/dt$_{max}$ when referring to a time derivative of an inverted impedance signal. In the context of the present invention, these subscripts merely identify the sign of the differentiated impedance signal. It is assumed that the dZ/dt$_{max}$ is always the positively largest one within the cycle, which is true physiologically. This dZ/dt$_{max}$ can be easily detected from the filtered (inverted) dZ/dt signal data due to the fact that it has the largest positive magnitude. The location of dZ/dt$_{max}$ ("C" in FIG. 2b) within the cycle is detected and stored as P. Variables "i" and "k" are initialized. Variable "i" is a discrete time variable and the location pointer of the first point of each 2*L period of data copied for processing while variable "k" is the kth value of the derived function S(k) depicted in FIG. 7. The first block of the flow chart of FIG. 6 indicates that $R_i$, $R_{i+1}$, M and P values are available.

In the second block, the first 2*L dZ/dt data points (starting from $R_i$ − D) are copied into a memory buffer. Note that L must be an order of two and is preferably at least sixteen. In other words, it can be sixteen, thirty-two, sixty-four, one-hundred-twenty-eight, etc. However, the relationship 2*L≦M must hold. Preferably, L equals thirty-two.

In the third block, each of these 2*L dZ/dt data points are multiplied by a selected window function (w[n]), preferably a Hamming window function, also with a length 2*L. The purpose is to smooth the dZ/dt data to reduce the edge effect. A Rectangular window function might alternatively be used. These two window functions are described below:

Rectangular w[n]=1 for i≦n≦i+2*L,
w[n]=0, otherwise;

Hamming w[n]=0.54−0.46 cos (2*$\pi$*n/M) for i≦n≦i+2*L,
w[n]=0, otherwise

In the fourth block, after the impedance data has been multiplied with the selected window function, a Fast Fourier Transform (FFT) is performed over these 2*L points. Note that the FFT routine requires 2*L points to return L points because the result has both real and imaginary parts and each part has L points.

Generally, the mathematical equation of the discrete Fourier transform for a frequency value that corresponds to n can be described as follows:

$$H[n] = \sum_{p=0}^{N-1} h[p]^{*}\exp(j^{*}2^{*}\pi^{*}n^{*}p/N)$$

where: h[p] is the input function, N is the number of input points (i.e., N=2*L), p is the discrete variable in time domain (expanding from 0 to N−1), n is the discrete variable in the frequency domain and equals (0,2*L−1) or $$\left(\frac{-N}{2}, \frac{N}{2}\right)$$

or (−L,L), all are equivalent.

The result of a complete Fourier transform is a complex array:

H[0],H[1], ... ,H[2*L−1].

where 2*L−1 corresponds to the one-half the sample frequency (i.e. 250 Hz) and 0 corresponds to zero frequency. Since the negative frequency part of the transform is only a mirror image of the positive part, it is usually dropped from the computation.

Here the input function is:

h[p]=w[p]*dZ/dt[p].

For a Hamming window function, the discrete Fourier transform is given by:

$$H[n] = \sum_{p=0}^{2*L-1} dZ/dt[p]*(0.54-0.46\cos(2*\pi*p/n))*\exp(j*2*\pi*n*p/2*L)$$

where $$n = \left(\frac{-N}{2}, \frac{N}{2}\right)$$

or $(-L,L)$. Note that the limit of p normally might be $R_i \leq p \leq R_i+2L-1$. However, since every 2*L duration is processed individually, as far as the Fourier transform is concerned, p always begins at 0.

The actual calculation is done by using the FFT computation algorithm to gain faster speed and the negative frequency part is not returned in the result. However, the principle and outcome are the same. Note that the values of H[n] are complex in format, i.e., real and imaginary. For $-L<n<L$, the set H generates two terms for every frequency, one for the real part, another for the imaginary part. Thus the actual result of this computation is an array of integers in the format:

H[0],H[1],H[2],H[3],H[4], ... H[2*L−2],H[2*L−1].

where H[0] and H[1] are the real and imaginary part of the 0 frequency, H[2] and H[3] are the real and imaginary part of the next immediately higher frequency, H[4] and H[5] for the subsequent immediately higher frequency, and so on.

In our application, only the magnitude of the FFT process components are used to generate the Spectrogram derived function S. That is also determined in the fourth block according to the equation:

$$FET(n)_{mag} = SQ\text{-}ROOT(H[2n]*H[2n]+H[2n+1]*H[2n+1])$$

and n=0,1, ... L−1.

Note that each of the magnitude points "n" corresponds to a particular frequency and thus reflects the distribution of that frequency in this 2*L portion of the signal. The bigger the magnitude is, the more that frequency contributes to this portion of the original dZ/dt signal. In this case, in each FFT process, 0–15 points or component values of the Spectrogram distribution are generated for deriving each point k of the Spectrogram derived function S. Points 0–15 correspond to $0-fo/2$ where fo is the sample frequency. Since we choose 2L=64, 0–31 represents $0-fo$, and 0–15 represents $$0 - \frac{fo}{2}.$$

The part $$\frac{fo}{2} - fo$$

is just the mirror image of $$0 - \frac{fo}{2}.$$

In the fifth block, an individual point S[k] of the Spectrogram derived function S(K) of FIG. 7 is determined. A certain range of frequencies contribute to the B, C and X peaks on the dZ/dt signal, and that frequency range is known to be between about 30–55 Hz, which roughly corresponds to frequency points between n=2 and n=3 (about 33.3 and 50 Hz for the example being described). This range is described in the FIG. 6 as frequency range $\omega1-\omega2$. Similarly, points n=0 to n=2 are described in the figure as frequency range $\omega0-\omega1$ (0 to about 33.3 Hz) and the points n=3 to n=15 as frequency range $\omega2-\omega3$ (about 50 to 250 Hz).

When $0 \leq i \leq P$ (P being the discrete time location of $dZ/dt_{max}$), the magnitudes of points between W1–W2 are combined by being summed together, and are normalized by the sum of the magnitude of points between W2–W3. When $P<i\leq M+L$, the magnitudes of points between W1–W2 are summed together and are normalized by the sum of the magnitude of points between W0–W2. S[k] contributes only one point to the time-frequency distribution derived function depicted in FIG. 7.

In the sixth block, k is increased by 1. However, i may be increased by a step size m to the right in the time domain. Note that $m<<2*L$. Thus, the second 2*L duration of the signal to be processed actually overlaps with the first duration.

Note that since every 2*L duration contributes only one point, if m, the step size, is bigger than one, then the number of resultant points actually shrinks by m times in the time domain. The result can be recovered back by the relationship:

S[j]=S[k] for (j=k; j≤k+m−1; j++)

Preferably, m is exactly one and no correction is needed.

In the seventh block, i is compared with M. If i is less than or equal to M, the whole process is repeated for the second duration for k=k+1 and i=i+1 until i>M.

The exemplary Spectrogram distribution derived function S is depicted in FIG. 7. S is a two-dimensional representation of the relative local power distribution for the selected subset of frequencies of interest associated with the cardiac event(s) in question. Specifically, in this example, the contributions from the frequencies 33.3–50 Hz, which are derived from the Spectrogram distribution of the time differential impedance signal, are combined by integrating the Spectrogram distribution over that selected frequency range of interest, or, more specifically in this example, by summing the discrete Spectrogram distribution contributions from the frequencies in that selected range of interest. Each block of the Spectrogram derived function S extending over the time interval from $R_i-0.2(R_{i+1}-R_i)$ to $R_{i+1}-0.2(R_{i+1}-R_i)$ preferably is analyzed after it is generated to identify at least one wave in the time-derivative impedance signal data dZ/dt(n) associated with the heartbeat $R_i$.

Preferably, the discrete time of occurrence "P" of the C wave of the heartbeat in question is first identified directly from the processed dZ/dt signal. The C wave has the greatest amplitude in the portion of the processed dZ/dt signal associated with the heartbeat $R_i$ (see FIG. 2b). The Spectrogram derived function data S(k) preferably is analyzed over the time interval in question spanning the single heartbeat $R_i$ to identify the maximum Spectrogram derived function data amplitude value, MAX, occurring over that interval. Proceeding backward in time through data of the Spectrogram derived function S(k) from the time of occurrence "P" of the C wave determined from the dZ/dt signal, the first identified Spectrogram derived function data value exceeding MAX/2 encountered occurs at the occurrence of the B wave or event and the discrete time of that occurrence is referred to as TMax1. The time of occurrence of the X wave is preferably determined using the time interval between the determined B and C events. Preferably, the X wave is identified as the first peak in the Spectrogram having a magnitude $\geq$ MAX/3 and occurring at least $|P-TMax1|$ seconds after the time of occurrence P of the C wave peak. The time of occurrence of that peak in the S(k) function is referred to as TMax3.

Normalization is not required but is performed for convenience in processing. It has been found through repeated experimentation and observation that the contributions of the frequencies in interest to the dZ/dt signal before P are noticeably less than the contributions from those frequencies after P. The normalization process and parameters described above have been empirically determined. It is firmly believed that other normalization bases, that comparison constants other than MAX/2, MAZ/3 could be derived and that the function S(k) could be analyzed without normalization in two blocks, O-P and P-M of each R—R interval.

Preferably, the system utilizes a VET= $|TMax3-TMax1|$, which corresponds to the absolute difference between the time of occurrences of the B and X events in the dZ/dt signal as determined in the above described manner from time-frequency analysis of the dZ/dt signal. Also in the preferred embodiment, $dZ/dt_{min}$ is determined to be the absolute magnitude of the change of the original dZ/dt signal between the times of the B and C events (TMax1 and P) as derived from the Spectrogram distribution derived data and the dZ/dt signal. VET and $dZ/dt_{min}$ can thereafter be plugged into either the Kubicek or Sramek equations.

After stroke volume (SV) is determined, for example by either the Kubicek or Sramek equations, cardiac output (CO) is determined by multiplying the stroke volume by the heart rate in beats per minute, which is preferably determined as described above from the EKG signal.

In comparison parallel tests on patients determining the cardiac output values obtained by the preferred system, utilizing the Kubicek model with a body weight correction factor, and the invasive Swan-Ganz thermodilution method, correlation coefficients of about 0.8 or more were found between the cardiac outputs determined by the two methods.

Preferably, the basic Kubicek equation was modified to take into account over/underweight of the various patients involved by multiplying the basic Kubicek equation by a size factor F determined empirically based upon ideal male and female weights.

Ideal female weight (IFW) in pounds was given by the relation:

$$IFW = 0.534*(height\ in\ inches) - 27.36$$

Ideal male weight (IMW) in pounds was given by the relation:

$$IMW = 0.534*(height\ in\ inches) - 17.36$$

Deviation of a patient's weight from the ideal weight is given by the relation:

$$deviation = (actual\ weight - idealweight)/ideal\ weight$$

The stroke volume calculated by the Kubicek model was adjusted up or down by a weight factor F, which had the following values for the following indicated deviation:
If deviation $< -0.50$,
F=0.10* Deviation+0.90
If $-0.5 \leq$ Deviation $<0.0$,
F=0.20* Deviation+1.00;
If $0.0 \leq$ Deviation $<0.6$,
F=0.43* Deviation+1.00; and
If $0.6 \leq$ Deviation,
F=0.60* Deviation+0.95.

Preferably, blood resistivity R in the Kubicek model was set equal to a constant 135 ohm-cm for male and 112 ohm-cm for female patients. It was found that when actual value of blood resistivity was calculated by the empirical equation:

$$R = 53.2e^{(0.022)HEM}$$

where HEM is the measured hematocrit, that significant underestimation resulted.

Alternatively, in place of either the Kubicek or Sramek model, the processor 30 of the system 20 can be configured to implement other models including the following relation of stroke volume:

$$SV = (L^2 F[weight]/C_c)(Z_o/Z_2 Z_3)$$

where $C_c$ is the mean thoracic conductivity, $Z_2$ is the impedance to ground (absolute impedance for absolute ground) sensed by one pair of voltage sensing electrodes, for example 22, and $Z_3$ is the absolute impedance to ground sensed by the remaining pair of voltage sensing electrode, for example 23, and $Z_o$ is the mean thoracic impedance previously identified. Again, it may be necessary to provide a scale factor, either F(weight) previously identified or another empirically determined factor, to adjust the relation for underweight and overweight individuals. The conductivity $C_c$ is the inverse of the resistivity.

The above proposed relation between stroke volume and impedance is derived from taking into account the concentric positioning of the generally circular heart within an elliptical pair of lungs within an elliptical thoracic wall in the region on which the voltage sensing electrodes are placed for generation of the impedance signals. The impedance values $Z_o$, $Z_2$ and $Z_3$ would be determined from the impedance signals at the peak of the R wave in the EKG signal, which preferably would be determined as has already been described.

The proposed relation continues to use the mean thoracic impedance $Z_o$, like both the Kubicek and Sramek models, and length L like Kubicek, but avoids the use of dZ/dt employed by both of those models. Consequently, this model has significantly reduced sensitivity to noise, motion artifact, respiratory cycles and ventilation effects. Again, it further can be adjusted to compensate for underweight and overweight individuals.

While the preferred system identifies heartbeats from adaptively processed EKG signals, standard, threshold determined EKG heartbeat and other devices and methods for determining heartbeats can be used in impedance signal processing. While one preferred time-frequency distribution and one preferred window function were discussed in detail, other time-frequency distributions and/or window functions might be employed in the present method and device, particularly when greater processing capability becomes available at comparable costs. Furthermore, at least some aspects of the invention lend themselves to parallel processing to improve upon the speed at which data processing and characteristic determination can be accomplished. The various aspects of the presently preferred embodiment are presently preferred based in large part upon data processing costs and the capability of current equipment. The adaptive identification of heartbeats and consequent heart rate determination by the present invention have their own independent value apart from their use in processing cardiac impedance signals. Other biological signals such as EEG, EMG, pulmonary pressure wave, etc. should also be adaptable to either the adaptive signal processing performed on the EKG signal or the time-frequency distribution processing performed on the impedance signal.

While one preferred embodiment of the system and methods of the present invention have been disclosed and at least one additional alternate suggested, one of ordinary skill in the art will recognize that changes may be made to the above-described embodiments of the invention without departing from the broad inventive concepts thereof. It is understood, therefore, that this invention is not limited to the particular embodiment disclosed but is intended to cover any modifications which are within the scope and spirit of the invention as defined by the appended claims.

We claim:

1. Apparatus for processing a time-derivative, thoracic impedance signal generated from a patient to identify events in the time-derivative impedance signal associated with beats of the patient's heart, the apparatus comprising:
   means for generating a time-frequency distribution of data from the time-derivative impedance signal for a selected portion of the time-derivative impedance signal spanning a single heartbeat of the patient; and
   means for identifying a time of occurrence of at least one cardiac event in the selected portion of said time-derivative impedance signal from the time-frequency distribution.

2. The apparatus of claim 1, wherein the identifying means comprises:
   means for determining a maximum amplitude value of the time-frequency distribution; and
   amplitude value identifying:
      means for identifying an amplitude value of the time-frequency distribution at least as great as a predetermined fractional value of the maximum amplitude value.

3. The apparatus of claim 2, wherein the amplitude value identifying means comprises:
   means for initially identifying a time of occurrence of a maximum amplitude value in the selected portion of the time-derivative impedance signal; and
   means for identifying a first amplitude value of the time-frequency distribution at least as great as the predetermined fractional value occurring in the time-frequency distribution most immediately preceding the time of occurrence of the maximum amplitude value of the time-derivative impedance signal.

4. The apparatus of claim 3, further comprising means for determining stroke volume of the patient during the single heartbeat from the difference between a time of occurrence of the first amplitude value of the time-frequency distribution and the time of occurrence of the maximum amplitude value of the time-derivative signal.

5. The apparatus of claim 3, further comprising means for identifying a second amplitude value of the time-frequency distribution at least as great as the predetermined fractional value and following the time of occurrence of the maximum amplitude value of the time-derivative signal by at least a predetermined time period.

6. The apparatus of claim 5, further comprising means for determining stroke volume of the patient during the single heartbeat from the difference between a time of occurrence of the first amplitude value of the time-frequency distribution and a time of occurrence of the second amplitude value of the time-frequency distribution.

7. The apparatus of claim 2, wherein the amplitude value identifying means comprises:
   means for initially identifying a time of occurrence of a maximum amplitude value in the selected portion of the time-derivative impedance signal; and
   means for identifying a second amplitude value of the time-frequency distribution at least as great as the predetermined fractional value and following the time of occurrence of the maximum amplitude value of the time-derivative signal by at least a predetermined time period.

8. The apparatus of claim 1, wherein the time-frequency distribution generating means comprises means for generating a Cohen derived time-frequency distribution of the selected portion of the time-derivative signal.

9. The apparatus of claim 8, wherein the time-frequency distribution generating means further comprises means for generating the distribution with a window function.

10. The apparatus of claim 1, further comprising:
    means for differentiating an electrocardiogram signal from the patient with respect to time, the means for differentiating having an input side;
    means for scaling the differentiated electrocardiogram signal non-linearly to emphasize amplitude peaks in the differentiated electrocardiogram signal;
    means for identifying a maximum amplitude value of the scaled signal occurring in a selected interval including several consecutive seconds of the scaled electrocardiogram signal;
    means for identifying each amplitude value of the scaled signal in the selected interval at least as great as a predetermined fraction of the maximum amplitude value; and
    means for generating the time-frequency distribution from a portion of the time-derivative signal spanning a time of occurrence of only one of the identified amplitude values of the scaled signal.

11. The apparatus of claim 10, further comprising means for transmitting a bi-level timing signal spanning the selected interval of the scaled signal and including level transitions corresponding in time to an occurrence of each of the identified amplitude values of the scaled signal during the selected interval.

12. The apparatus of claim 10, further comprising means for filtering the electrocardiogram signal to remove low frequency components of the signal from patient movement and high frequency components of the signal from sources of external electrical interference, said filtering means being connected to said input side of the differentiating means.

13. The apparatus of claim 12, wherein the filtering means comprises means for passing data of the electrocardiogram signal through a high-pass filter to eliminate frequency components of about five hertz or less from the signal data to form high pass filtered data.

14. The apparatus of claim 13, wherein the filtering means further comprises means for passing the high-pass filtered data through a low-pass filter to at least eliminate components of about fifty hertz or more from the high-pass filtered data.

15. The apparatus of claim 13, wherein the passing means further comprises means for passing said filtered data through a low-pass filter to at least eliminate components of about forty hertz or more from the high-pass filtered data.

16. The apparatus of claim 12, further comprising means for digitizing the electrocardiogram signal, and wherein the filtering means comprises means for passing data of the digitized electrocardiogram signal through an all-integer coefficient filter.

17. The apparatus of claim 10, further comprising:
means for generating a coefficient of variation for the amplitude values of the scaled signal identified from the selected interval;
means for comparing the coefficient of variation to a predetermined value; and
means for transmitting a bi-level timing signal spanning the selected interval and including level transitions corresponding in time to a time of occurrence of each of the identified amplitude values of the scaled signal during the selected interval only if the coefficient of variation for the interval is at least less than a predetermined fractional value.

18. The apparatus of claim 1, further comprising means for filtering the time-derivative signal to remove low frequency components from patient movements and higher frequency components from sources of electrical interference external to the patient, and wherein the generating means comprises means for generating the time-frequency distribution from the filtered time-derivative signal.

19. The apparatus of claim 18, wherein the filtering means comprises means for removing frequency components of about 5 hertz or less and about 50 hertz or more from the time-derivative impedance signal.

20. The apparatus of claim 1, wherein the identifying means comprises:
means for combining a subset of components of the time-frequency distribution from the selected portion of the time-derivative impedance signal, the subset of components representing contributions to the time-derivative impedance signal from a selected range of frequencies associated with cardiac events occurring during the beating of the patient's heart, the selected range of frequencies being less than a larger range of frequencies, including the selected range, contributing components to the time-derivative impedance signal;
means for determining a maximum amplitude value of an integrated time-frequency distribution associated with the selected portion of the time-derivative impedance signal; and
means for identifying an amplitude value of the integrated time-frequency distribution associated with the selected portion of the time derivative impedance signal, the identified amplitude being at least as great as a predetermined fractional value of the maximum amplitude value.

21. The apparatus of claim 20, wherein the amplitude value identifying means comprises:
means for initially identifying a time of occurence of a maximum amplitude value in the selected portion of the time-derivative impedance signal; and
means for identifying a first amplitude value of the integrated time-frequency distribution at least as great as the predetermined fractional value, which occurs in the integrated time-frequency distribution most immediately preceding in time the time of occurrence of the maximum amplitude value identified in the selected portion of the time-derivative impedance signal.

22. The apparatus of claim 21, further comprising means for determining stroke volume of the patient during the single heartbeat from a difference between a time of occurrence of the first amplitude value of the integrated time-frequency distribution and the time of occurrence of the maximum amplitude value of the time-derivative impedance signal.

23. The apparatus of claim 22, further comprising means for identifying a second amplitude value of the integrated time-frequency distribution at least as great as the predetermined fractional value and following the time of occurrence of the maximum amplitude value of the time-derivative signal by at least a predetermined time period.

24. The apparatus of claim 23, further comprising means for determining stroke volume of the patient during the single heartbeat from a difference between the time of occurence of the first amplitude value of the integrated time-frequency distribution and a time of occurrence of the second amplitude value of the integrated time-frequency distribution.

25. The apparatus of claim 20, wherein the amplitude value identifying means comprises:
means for initially identifying a time of occurrence of a maximum amplitude value in the selected portion of the time-derivative impedance signal; and
means for identifying a second amplitude value of the integrated time-frequency distribution, the second amplitude value being at least as great as the predetermined fractional value and the second amplitude value following a time of occurrence of the maximum amplitude value in the selected portion of the time-derivative impedance signal by at least a predetermined time period.

26. The apparatus of claim 20, wherein the integrating means comprises means for combining contributions to the time-frequency distribution of data in a range of about 30 Hz to about 55 Hz.

* * * * *